United States Patent [19]

Radunz et al.

[11] Patent Number: 5,026,642

[45] Date of Patent: Jun. 25, 1991

[54] PROCESS FOR THE ENZYMATIC PRODUCTION OF KETONES

[75] Inventors: Hans-Eckart Radunz, Mühltal; Harry Schwartz, Hochheim/Main; Martin Heinrich, Darmstadt, all of Fed. Rep. of Germany

[73] Assignee: Merck Patent Gesellschaft mit Beschränkter Haftung, Darmstadt, Fed. Rep. of Germany

[21] Appl. No.: 223,051

[22] Filed: Jul. 22, 1988

[30] Foreign Application Priority Data

Jul. 22, 1987 [DE]  Fed. Rep. of Germany ....... 3724197

[51] Int. Cl.$^5$ ................ C07C 125/065; C07C 101/30; C12P 7/02; C12P 7/42
[52] U.S. Cl. ................................ 435/117; 435/118; 435/119; 435/120; 435/121; 435/122; 435/123; 435/124; 435/125; 435/126; 435/127; 435/128; 435/155; 435/190; 435/280; 435/930; 435/942
[58] Field of Search ............... 435/117, 118, 119, 120, 435/121, 122, 123, 124, 125, 126, 127, 128, 280, 155, 190, 920

[56] References Cited

PUBLICATIONS

"Synthesen der (3S,4S)-4-Amino-3-Hydroxy-6-Methylheptansaure und Einiger Derivate", Steulmann et al., Liebigs Ann. Chem. 1975, pp. 2245-2250.
"Yeast Reduction of Ethyl Acetoacetate: (S)-(+)--Ethyl 3-Hydroxybutanoate", Seeback et al., Organic Synthesis, 63, pp. 1-9 (1985).
"Stereochemical Control in Microbial Recution 4. Effect of Cultivation Conditions on the Recution of β-Keto Esters by Methylotrophic Yeasts", Ushio et al., Tetrahedron Letters, vol. 27, No. 23, pp. 2657-2660 (1986).
"Substrate Modification as a Means of Enhancing the Enantioselectivity of Microbial Reductions of β-Keto Esters. An (R)- or (S)-1,3,5-Trihydroxypentane Synthon", Brooks et al., Journal of Organic Chemistry, 1987, 52, pp. 192-196.
R. Scheffold, ed., Modern Synthetic Methods 1989, pp. 54-55, 106-107.

Primary Examiner—Herbert J. Lilling
Attorney, Agent, or Firm—Millen, White & Zelano

[57] ABSTRACT

In a process for the reduction of ketones, the keto compounds are enantioselectively reduced to give secondary alcohols by means of microorganisms. Keto compounds of the formula

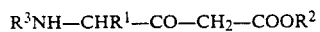

$R^3NH-CHR^1-CO-CH_2-COOR^2$ in which $R^1$, $R^2$ and $R^3$ have the meanings defined herein are used as starting compounds.

24 Claims, No Drawings

PROCESS FOR THE ENZYMATIC PRODUCTION OF KETONES

BACKGROUND OF THE INVENTION

The invention relates to a microbial process for the enantioselective reduction of keto compounds of the formula I $$R^3HN-CHR^1-CO-CH_2-COOR^2 \quad\quad I$$

in which

R$^1$ is A, Ar, Ar-alkyl, Het, Het-alkyl, cycloalkyl having 3–7 C atoms which is unsubstituted or mono- or polysubstituted by A, AO and/or Hal, cycloalkylalkyl having 4–11 C atoms or bicycloalkyl having 7–14 C atoms or bicycloalkylalkyl having 8–18 C atoms, R$^2$ is H or alkyl having 1–5 C atoms, R$^3$ is H, benzyl, triphenylmethyl, benzyloxycarbonyl, tert.-butyloxycarbonyl or 9-fluorenylmethoxycarbonyl, Ar is phenyl which is unsubstituted or mono- or polysubstituted by A, AO, Hal, CF$_3$, HO, hydroxyalkyl having 1–8 C atoms, H$_2$N and/or aminoalkyl having 1–8 C atoms or is unsubstituted naphthyl, Het is a saturated or unsaturated 5- or 6-membered heterocyclic radical having 1–4 N, O and/or S atoms which can be fused with a benzene ring and/or mono- or polysubstituted by A, AO, Hal, CF$_3$, HO, O$_2$N, carbonyl oxygen, H$_2$N, HAN, A$_2$N, AcNH, AS, ASO, ASO$_2$, AOOC, CN, H$_2$NCO, HOOC, H$_2$NSO$_2$, ASO$_2$NH, Ar, Ar-alkenyl, hydroxyalkyl and/or aminoalkyl each having 1–8 C atoms and/or whose N and/or S heteroatoms can also be oxidized, Hal is F, Cl, Br or I, Ac is A—CO—, Ar—CO— or A—NH—CO— and A is alkyl having 1–8 C atoms, to give the corresponding secondary alcohols which are important intermediates in the synthesis of pharmacologically useful renin inhibitors.

Compounds of the formula II $$R^3NH-CHR^1-CHOH-CH_2-COOR^2 \quad\quad II$$

in which R$^1$ to R$^3$ have the meanings mentioned, are derivatives of the naturally occurring γ-amino acid statine. To be effective for renin inhibition, the OH group at the β-C atom of the compounds of the formula II must have the S configuration as must the amino group at the γ-C atom. Suitable compounds for preparing the secondary alcohols are preferably the corresponding keto compounds of the formula I. The reduction of these keto compounds by known standard methods, for example using LiAlH$_4$, NaBH$_4$, Na/NH$_3$ or Li/NH$_3$, can only be achieved in very poor yields, due to the easier enolizability of the oxygen on the β-C atom. Reduction with Raney nickel causes an increase in the yield (Steulmann and Klostermeyer, Liebigs Ann.Chem., p. 2245–2250 (1975)). However, all these reductions of such β-keto compounds have in common the fact that a diastereomeric mixture consisting of the R and S form of the relevant secondary alcohols is formed, in most cases in equal parts. This means that the completed reduction must usually be followed by a separation of diastereomers which, in most cases, is expensive. This again leads to losses in yield which are often substantial. More recently, yeasts which are able to reduce largely enantioselectively have sometimes been used for the reduction of keto compounds, in particular of β-keto esters (for example Seebach et al., Org. Synth. 63, 1–9 (1985); Ushio et al., Tetrahedron Lett. Vol. 27, No. 23, 2657–2660 (1986); Brooks et al., J.Org. Chem. 52, 192–196 (1987)). However, in these systems a strong influence of the groups adjacent to the reaction center can often be observed: small changes can lead to substantially poorer yields and unfavorable enantiomer ratios, with the result that so far it has only been possible to reduce a limited range of fairly specific β-keto compounds with satisfactory enantioselectivity by means of yeasts. Often, even the "wrong" enantiomer is obtained.

SUMMARY OF THE INVENTION

It is an object of the invention to provide a process which makes it possible to prepare useful compounds of the formula II in high yields stereospecifically and in a simple and economical manner.

Upon further study of the specification and appended claims, further objects and advantages of this invention will become apparent to those skilled in the art.

Surprisingly, it has been found that the β-keto compounds of the formula I can be reduced by means of microorganisms, in particular yeasts, in good yields to give the biologically active, secondary alcohols of the formula II having an S configuration on the β-C atom. This achievement was not foreseeable from the prior art, in particular in view of the special and in part reactive groups which the starting compounds contain.

The invention therefore provides a process for the enantioselective reduction of keto compounds to give secondary alcohols by means of microorganisms, characterized in that compounds of the formula I are used as starting materials.

The invention further provides the use of the compounds of the formula II, which are prepared by reduction of compounds of the formula I by means of microorganisms, in the synthesis of renin inhibitors containing the structural element —NH—CH—CHOH—CH$_2$—CO—

Hereinbefore and hereinafter the radicals R$^1$, R$^2$, R$^3$, Ar, Het, Hal, Ac and A have the meanings mentioned, unless explicitly noted otherwise.

In the above formulae, A has 1–8, preferably 1, 2, 3 or 4, C atoms. A preferably is methyl, furthermore ethyl, propyl, isopropyl, butyl, isobutyl, sec.-butyl or tert.butyl, furthermore also pentyl, 1-, 2- or 3-methylbutyl, 1-, 1,2- or 2,2-dimethylpropyl, I-ethylpropyl, hexyl, 1-, 2-, 3- or 4-methylpentyl, 1,1-1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl.

Typically, all alkyl portions mentioned have up to 8 carbon atoms, including the alkenyl and alkyl portions of Ar-alkenyl, Ar-alkyl, Het-alkyl and hydroxyalkyl.

Cycloalkyl preferably is cyclopropyl, cyclobutyl, cyclopentyl, cyclohexyl or cycloheptyl. Substituted cycloalkyl preferably is 1-, 2- or 3-methylcyclopentyl, 1-, 2-, 3- or 4-methylcyclohexyl or 4-tert.-butylcyclohexyl, the substituents preferably being arranged trans to one another.

Accordingly, cycloalkylalkyl preferably is cyclopropylmethyl, 2-cyclopropylethyl, cyclobutylmethyl, 2-cyclobutylethyl, cyclopentylmethyl, 2-cyclopentylethyl, cyclohexylmethyl or 2-cyclohexylethyl, but also, for example, 1-, 2- or 3-methylcyclopentylmethyl, 1-, 2-, 3-, 4-methylcyclohexylmethyl or 4-tert.-butylcyclohexylmethyl, the substituents preferably being arranged trans to one another.

Bicycloalkyl preferably is 1- or 2-decalyl, 2-bicyclo[2,2,1]heptyl or 6,6-dimethyl-2-bicyclo[3,1,1]heptyl.

Hal preferably is F, Cl or Br, but also I.

Ac preferably is A-CO- such as acetyl, propionyl or butyryl, Ar-CO- such as benzoyl, o-, m- or p-methoxybenzoyl or 3,4-dimethoxybenzoyl, A-NH-CO- such as NZO methyl- or N-ethylcarbamoyl.

Ar preferably is phenyl, furthermore preferably o-, m-or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or Z5 p-trifluoromethylphenyl, o-, m- or p-hydroxyphenyl, o-, mor p-hydroxymethylphenyl, 2,3-, 2,4-, 2,5-, 2,6-, 3,4- or 3,5-dimethoxyphenyl, 3,4,5-trimethoxyphenyl, o-, m- or p-aminophenyl, o-, m- or p-aminomethylphenyl or 1- or 2-naphthyl.

Accordingly, Ar-alkyl preferably is benzyl, 1- or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxybenzyl, 1- or 2-o-, -m- Or -p-methoxyphenylethyl, o-, m- or p-fluorobenzyl, 1or 2-o-, -m- or -p-fluorophenylethyl, o-, m- or p-chlorobenzyl, 1- or 2-o-, -m- or -p-chlorophenylethyl, o-, mor p-bromobenzyl, 1- or 2-o-, -m- or -p-bromophenylethyl, o-, m- or p-iodobenzyl, 1- or 2-o-, -m-or -p-iodophenylethyl, o-, m-or p-trifluoromethylbenzyl, o-, m-or p-hydroxybenzyl, o-, m- or p-hydroxymethylbenzyl, 2,3-, 2,4-, 2,5-, 2,6-, 3,4- or 3,5-dimethoxybenzyl, 3,4,5-trimethoxybenzyl, o-, m- or p-aminobenzyl, o-, m- or p-aminomethylbenzyl or 1- or 2-naphthylmethyl.

Het preferably is 2- or 3-furyl, 2- or 3-thienyl, 1-, 2or 3-pyrryl, 1-, 2-, 4- or 5-imidazolyl, 1-, 3-, 4-or 5pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidyl, furthermore preferably 1,2,3-triazol-1-, -4- or -5-yl, 1,2,4-triazol-1-, -3- or -5-yl, 1- or 5-tetrazolyl, 1,2,3-oxadiazol-4-or -5-yl, 1,2,4-oxadiazol-3- or -5-yl, 1,3,4-thiadiazol-2-or -5-yl, 1,.2,4-thiadiazol-3- or -5-yl, 2,1,5-thiadiazol-3- or -4-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6 or 7-benzofuryl, 2-, 3-, 4-, 5- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazylyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, or 8-isoquinolyl, 1-, 2-, 3-, 4- or 9-carbazolyl, 1-, 2-, 3-, 4-, 5-, 6-, 7-, 8- or 9-acridfnyl, 3-, 4-, 5-, 6-, 7or 8-cinnolyl, 2-, 4-, 5-, 6-, 7- or 8-quinazolyl. The heterocyclic radicals can also be partially or completely hydrogenated. Het can therefore, for example, also be 2,3-dihydro-2-, -3-, -4- or -5-furyl, 2,5-dihydro-2-, -3-, -4- or -5-furyl, tetrahydro-2- or -3-furyl, tetrahydro-2or -3-thienyl, 2,3-dihydro-1-, -2-, -3-, -4- or -5-pyrryl, 2,5-dihydro-1-, -2-, -3-, -4- or -5-pyrryl, 1-, 2- or 3pyrrolidinyl, tetrahydro-1-, -2- or -4-imidazolyl, 2,3-dihydro-1-, -2-, -3-, -4- or -5-pyrazolyl, 2,5-dihydro-1-, -2-, -3-, -4- or -5-pyrazolyl, tetrahydro-1-, -3-, or -4pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3or 4-piperidinyl, 2-, 3- or 4-morpholinyl, tetrahydro-2-, -3- or -4-pyranyl, 1,4-dioxanyl, 1,3-dioxan-2-, -4- or -5yl, hexahydro-1-, -3- or -4-pyridazinyl, hexahydro-1-, -2-, -4- or -5-pyrimidyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or 8isoquinolyl.

The heterocyclic radicals can also be substituted as mentioned. This means that Het can preferably also be: 2-amino-4-thiazolyl, 4-carboxy-2-thiazolyl, 4-carbamoyl2-thiazolyl, 4-(2-aminoethyl)-2-thiazolyl, 2-amino-5,6-dimethyl-3-pyrazinyl, 4-carbamoyl-piperidino, furthermore for example 3-, 4- or 5-methyl-2-furyl, 2-, 4- or 5-methyl3-furyl, 2,4-dimethyl-3-furyl, 5-nitro-2-furyl, 5-styryl-2furyl, 3-, 4- or 5-methyl-2-thienyl, 2-, 4- or 5-methyl-3thienyl, 3-methyl-5-tert.-butyl-2-thienyl, 5-chloro-2thienyl, 5-phenyl-2- or -3-thienyl, 1-, 3-, 4- or 5-methyl2-pyrryl, 1-methyl-4- or -5-nitro-2-pyrryl, 3,5-dimethyl-4-ethyl-2-pyrryl, 4-methyl-5-pyrazolyl, 4- or 5-methyl-2thiazolyl, 2- or 5-methyl-4-thiazolyl, 2- or 4-methyl-5thiazolyl, 2-pyridyl, 2-, 4-, 5- or 6-methyl-3-pyridyl, 2- or 3-methyl4-pyridyl, 3-, 4-, 5-or 6-chloro-2-pyridyl, 2-, 4-, 5- or 6-chloro-3-pyridyl, 2- 3-chloro-4-pyridyl, 2,6-dichloropyridyl, 2-hydroxy-3-, -4-, -5- or -6-pyridyl (=1H-2-pyridon-3-, -4-, -5- or -6-yl), 5-phenyl-1H-2-pyridon-3-yl, 5-p-methoxyphenyl-1H-2-pyridon-3-yl, 2-methyl-3-hydroxy-4-hydroxymethyl-5-pyridyl, 2-hydroxy-4-amino-6-methyl-3pyridyl, 3-N'-methylureido-1H-4-pyridon-5-yl, 5- or 6-methyl-4-pyrimidyl, 2,6-dihydroxy-4-pyrimidyl, 5-chloro-2-methyl-4-pyrimidyl, 2-methyl-4-amino-5-pyrimidyl, 3-methyl2-benzofuryl, 2-ethyl-3-benzofuryl, 7-methyl-2-benzothienyl, 1-, 2-, 4-, 5-, 6- or 7-methyl-3-indolyl, 1-methyl-5- or -6-benzimidazolyl, 1-ethyl-5- or -6-benzimidazolyl, 3-, 4-, 5-, 6-, 7- or 8-hydroxy-2-quinolyl.

R¹ is preferably benzyl, cyclohexylmethyl, 4-methylcyclohexylmethyl, 4-tert.-butylcyclohexylmethyl, and also phenyl, p-chlorobenzyl, 2-phenylethyl, 2-cyclohexylethyl, 1- or 2-naphthylmethyl and furthermore methyl, ethyl, propyl, isopropyl, butyl, isobutyl, sec.-butyl, pentyl or 2- or 3-methylbutyl.

R² is preferably alkyl having 1-3 C atoms, that is methyl, ethyl, propyl or isopropyl R³ is preferably H, benzyloxycarbonyl or tert.-butyl-.oxycarbonyl.

The keto compounds of the formula I (hereinafter "ketostatines") which serve as starting compounds are either known or can be prepared in a manner known per se by standard methods of organic chemistry. Preferably, esters of α-amino acids of the formula IV

R³HN—CHR¹—COOR⁴    IV in which R¹ and R³ have the meanings mentioned and R⁴ is an easily removable carboxyl-protective group, for example methyl, ethyl, benzyl or phenacyl are condensed with malonic acid derivatives of the formula V

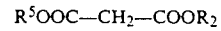
R⁵OOC—CH₂—COOR₂    V in which R² has the meaning mentioned and

R⁵ is H, alkyl or MgBr⁺, hydrolyzed and decarboxylated. The reaction conditions are those of the customary malonic ester syntheses. A comparable synthesis of ethyl 4-amino-3-oxo-6-methylheptanoate has been described in detail in Steulmann and Klostermeyer, loc. cit.

If R³ is not H, its function is that of a re-removable amino-protective group. For the reduction according to the invention of the ketostatines by means of microorganisms, the presence of an amino-protective group - in most cases, in contrast to the conventional chemical reduction - is not required. However, for certain work-up techniques following the reduction, in particular, if the reaction product is to be transferred to organic phases, the presence of an amino-protective group is very useful, since the unprotected product is, as a rule, water-soluble. If the reduction of the ketostatine is carried out in the presence of an amino-protective group, this group must not contain a keto group which can be reduced by microorganisms. The incorporation of the amino-protective group into the ketostatines is carried out by standard methods known from the literature. For this purpose, tert.-butyloxycarbonyl (BOC) or benzyloxycarbonyl (Z) are preferably used.

Suitable microorganisms are in general all those species which contain enzymes which transfer hydrogen (dehydrogenases). Particular preference is given to yeasts, since, on the one hand, they have relatively high dehydrogenase activities, and, on the other hand, are readily available and require only simple cultural conditions.

Suitable yeasts are preferably the genera Saccharomyces, Candida, Hansenula, Pullularia, Torulopsis or Williopsis. Particular preference is given to yeasts of the genus Hansenula, in particular the genera Hansenula ciferrii, Hansenula saturnus or Hansenula anomala. The preferred yeasts are either commercially available or accessible to the general public via a specially authorized depository institution (for example Hansenula ciferrii: DSM 70780; Hansenula saturnus: DSM 70278; Saccharomyces uvarum: DSM 70547; Torulopsis candida: DSM 70590 or Hansenula anomala: 15 DSM 70130).

The culturing of microorganisms and the production of cell mass for experimental purposes is carried out in suitable customary media by known methods. The yeasts which are preferred in the process according to the invention, in particular those of the genus Hansenula, are preferably kept in a yeast-extract-peptone medium (YEP) having, for example, the following composition: peptone (2%), glucose (2%), $KH_2PO_4$ (0.1%), agar (2%), yeast extract (1%); pH: 6.5. The production of cell mass is preferably carried out in a medium consisting of 0.3% of yeast extract, 0.3% of malt extract, 2% of glucose and 0.5% of peptone (pH =6.5). The amounts given are only an example. This medium is developed into a 20-30-hour old culture in a known manner. After the culture is completed, the cells are preferably centrifuged off and deep-frozen until they are reacted.

In the process according to the invention, the ketostatines used are preferably compounds of the formula I in which $R^1$ is benzyl, 4-methylcyclohexylmethyl or 4-tert.-butylcyclohexylmethyl, $R^2$ is methyl or ethyl and $R^3$ is H or an amino-protective group, as mentioned above.

Preferably, the process according to the invention is carried out as follows. The appropriate ketostatine is, in particular if it contains an amino-protective group, dissolved in ethanol, the ethanol concentration being between 3-10% and the ketostatine concentration being 0.05-0.5%, preferably 0.1-0.2%, based on the incubation volume. The ethanolic ketostatine solution is added to an aqueous 5-30%, preferably 10-20%, glucose solution in which the deepfrozen yeast cells had previously been suspended. The yeast concentration varies between 0.5 and 5%, but preferably between 1 and 2%. The reduction is carried out with continuous stirring between 25 and 30 °C., preferably at 28° C., under fermenting conditions or with slight ventilation. Preference is given to the latter, in particular if the process according to the invention is carried out on an industrial scale. The duration of incubation is between 24 and 84 hours, preferably between 48 and 72 hours.

In a further embodiment of the inventive process, the reduction can also be carried out with growing cells instead of dormant ones—as described—which has the advantage that the preculturing becomes unnecessary. ketostatine dissolved in a minimum amount of ethanol is added to a cell suspension in a customary growth medium according to the literature consisting, for example, of glucose (5%), m-inositol (0.004%), $KH_2PO_4$ (0.1%), $MgSO_4$ (0.1%), potassium hydrogen tartrate (0.45%), trace elements and vitamins (pH 5-6), and the reduction is carried out under the same conditions as described above for dormant cells.

Work-up, purification and analysis of the secondary alcohol formed is identical for dormant and growing cells. If the educt/product contains an amino-protective group, the cell suspension is extracted several times with an organic solvent, for example ethyl acetate, dichloromethane, diethyl ether or butyl methyl ether. If necessary, another purification, for example with silica gel, can follow in a manner known per se. Since, according to the invention, a large excess of one enantiomer is formed, a purification can also be achieved by selective crystallization using known methods. For this purpose, the organic phase is concentrated until a residue is obtained and dissolved in an organic solvent suitable for crystallization and recrystallization and crystallized. Detection and determination of the enantiomeric ratio (R and S form) can be carried out in a manner known per se, for example by thin-layer chromatography or HPLC. If desired, the amino-protective group can be removed from the final product in a manner known per se.

If the relevant ketostatine does not contain an amino-protective group ($R^3$=H), an extraction by means of organic solvents after the completed reduction is generally not possible, since the alcohol formed is water-soluble in its amino-unprotected form and a prior alkalization leads to cyclization. However, the corresponding alcohol can be obtained directly from the reaction suspension by separating off the cells followed by freeze-drying. Purification and detection correspond to the protected form.

In a further embodiment of the process according to the invention, the reduction of the ketostatine can be carried out by means of immobilized cells. In this process, the cells are incorporated in a known manner into a conventional support matrix, for example a polyacrylamide gel. The support matrix is comminuted and is used instead of "free" cells for the reduction under otherwise unchanged conditions described above. This reaction can be carried out batchwise or in a column operation. Even multiple use of the gel charged with the cells is possible, in which case, however, the reducing efficiency of the immobilized cells is somewhat diminished. The extraction or purification is carried out from the eluate after its removal from the gel in the manner described above.

Finally, the reduction of the corresponding ketostatine by the process according to the invention, can also be carried out by means of a cell-free extract. For this purpose, the cells are homogenized or digested in a known manner. To the cell-free extract obtained therefrom, which contains the hydrogen-transferring enzymes and cofactors in dissolved form, are added glucose and ketostatine the concentrations mentioned, and the reduction is completed between 25 and 30° C. over a period of several hours. The subsequent procedure is carried out as described.

The reduction of ketones of the formula I to give the secondary alcohols of the formula II by means of reducing microorganisms, in particular yeasts, leads to the following advantageous results: the yield in alcohol varies between 50 and 98%, based on the educt, depending on the microorganism used, on the ketostatine used and the embodiment. The best yields using the extraction process are obtained by ketostatines of the formula I in which $R^1$ is benzyl and $R^2$ is methyl, followed by compounds in which $R^1$ is 4-methylcyclohexylmethyl and $R^1$ is 4-tert.-butylcyclohexylmethyl and in which, in each case, $R^2$ is methyl. The yields for the unprotected compounds are also very good. Based on the alcohols formed, 90-99% of them, preferably 95-98%, are present in the biologically active S configuration (at the C atom bearing the OH group) while the remaining compounds have the R configuration. Of the yeasts used, the genus Hansenula and therein, in particular, the genera Hansenula ciferrii, Hansenula saturnus and Hansenula anomala give the highest yields altogether and the highest yields of 3S enantiomers. The type of embodiment with respect to yield and enantiomeric ratio in general plays only a minor role.

The secondary alcohols of the formula II prepared by the process according to the invention are important intermediates in the synthesis of renin inhibitors, which can be used in pharmacology as effective and useful hypotensive agents. So far, almost all known renin inhibitors have the statine structural element

The preparation of renin inhibitors containing this structural element starting from the secondary alcohols of formula II is described for example in U.S. Pat. Nos. 4,709,010 and 4,721,776.

A known keto compound of formula I in which $R^1$ is isobutyl, $R^2=R^3$ is H, is described in "Steulmann and Klostermeyer, Liebigs Ann. Chem., p. 2245-2250 (1975)."

A known compound of the secondary alcohols of formula II is for example "statine" (Merck & Co.-Index 1983 No. 8652).

In the process according to the invention, the conversion of keto compounds to secondary alcohols is generally at least about 50%, preferably at least about 60%, and especially 70 to 90%. In the resultant product mixture, the enantiomeric ratio of S/R configuration is at least about 9/1, preferably at least about 20/1, and especially 20/1 to 50/1.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

EXAMPLE 1

In a 500-ml Erlenmeyer flask, 2 g of yeast cells of the genus Hansenula ciferrii (DSM 70780) are suspended in 100 ml of 20% glucose solution. After onset of fermentation 200 mg of methyl 5-phenyl-4(S)-BOC-amino-3-oxo valerate dissolved in 5 ml of ethanol are added to the mixture. The incubation is carried out at 28° C. with continuous stirring. After 48 hours, a further 10 g of glucose are added, and the incubation is continued for another 24 hours. The incubation is stopped by the addition of ethyl acetate, and the mixture is stirred for another hour. The phases are separated, and the organic phase is dried with sodium sulfate and concentrated. The residue is taken up in cyclohexane/tert.-butyl methyl ether and chromatographed over silica gel. Eluent: cyclohexane/tert.-butyl methyl ether (1:1). To confirm the conversion and to determine the enantiomeric ratio, a sample of educt and product are chromatographed by means of HPLC as follows. Column: RP 8, mobile phase: $CH_3CN/0.1\ M\ NaH_2PO_4$ (1:1), detection at 220 nm. This gives methyl 5-phenyl-4(S)-BOC-amino-3(S)-hydroxyvalerate; enantiomeric purity: 97%.

EXAMPLE 2

100 g of cultured yeast cells of the genus Hansenula saturnus (DSM 70278) are suspended in 10 liters of 10% glucose solution, and 10 g of methyl 5-phenyl-4(S)-BOC-amino-3-oxo valerate dissolved in 100 ml of ethanol are added to this suspension. The incubation is carried out with slight ventilation and continuous stirring at 28° C.

The incubation is stopped after 72 hours by the addition of a total of 5 liters of ethyl acetate. The organic phase is filtered off with suction over kieselguhr, dried with sodium sulfate and recrystallized. This gives methyl 5-phenyl-4(S)-BOC-amino-3(S)-hydroxyvalerate; enantiomeric purity: 95%.

EXAMPLE 3

To 150 mg of methyl 5-(4-methylcyclohexyl)-4(S)-BOC-amino3-oxovalerate (dissolved in 5 ml of ethanol) are added 100 ml of 15% glucose solution which contains 1.5 g of yeast cells of the genus Hansenula ciferrii, and the mixture is reacted analogously to Example 1. This gives methyl 5-(4-methylcyclohexyl)-4(S)-BOC-amino-3(S)-hydroxyvalerate; enantiomeric purity: 80%.

EXAMPLE 4

Analogously to Example 1, 200 mg of 5-(4-tert.-butylcyclohexyl)-4(S)-BOC-amino-3-oxovaleric acid are reacted -1 with 2 g of commercial baker's yeast (Saccharomyces cerevisiae) and worked up. This gives 5-(4-tert.-butyl-cyclohexyl)-4(S)-BOC-amino-3S-hydroxyvaleric acid; enantiomeric purity: 64%.

EXAMPLE 5

10 g of cultured yeast cells of the genus Hansenula saturnus are suspended in 1 liter of 15% glucose solution and 1 g of methyl 5-phenyl-4(S)-amino-3-oxovalerate (dissolved in 20 ml of ethanol) are added. The incubation conditions correspond to those of Example 1. After the incubation is completed, the yeast cells are centrifuged off and subsequently washed with water. The combined aqueous supernatants are subsequently freeze-dried. This gives methyl 5-phenyl-4(S)-amino-3(S)-hydroxyvalerate; enantiomeric purity: 90%.

EXAMPLE 6

1 g of cells from Hansenula ciferrii are suspended in 1 ml of 0.9% NaCl solution, and the suspension is cooled to 4° C. These yeast cells are mixed with equal parts of a solution of 750 mg of acrylamide and 40 mg of N,N'-methylenebisacrylamide in 2.4 ml of H20. The polymerization is initiated by adding 0.1 ml of a 25% β-dimethylaminopropionitrile solution and 0.5 ml of a 1% potassium peroxodisulfate solution. After the polymerization is completed, the gel is comminuted and is used instead of "free" yeast cells analogously to Example 1 for the reduction of 100 mg of methyl 5-phenyl-4(S)-BOC-amino-3-oxovalerate. This gives methyl 5-phenyl-4(S)-BOC-amino-3(S)-hydroxyvalerate; enantiomeric purity: 97%.

EXAMPLE 7

2 ml of 0.1 N tris/HCl buffer, pH 7.5, and 4 g of glass beads (0.45-0.50 mm in diameter) are added to 2 g of commercial baker's yeast, and the mixture is digested in a cell homogenizer at about 4,000 rpm at 0° to 4° C. Glass beads and cell fragments are centrifuged off for 20 minutes at about 6,000 xg. 20% of glucose (weight volume) and 0.1% of methyl 5-phenyl-4(S)-amino-3-oxovalerate are added to the extract which is now cell-free. With gentle stirring, the mixture is incubated at 28° C. for several hours. After the incubation is completed, the soluble proteins are precipitated with acetone; the supernatant is then extracted several times with ethyl acetate. Denatured protein is centrifuged off from the aqueous phase and washed with water. The combined aqueous extracts are freezedried. This gives methyl 5-phenyl-4(S)-amino-3(S)-hydroxyvalerate; enantiomeric purity: 92%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the synthesis of a renin inhibiting agent containing the structural element

using as an intermediate a secondary alcohol according to the formula

R³NH—CHR¹—CHOH—CH₂—COOR², the improvement wherein said secondary alcohol was prepared according to the process comprising reducing a keto compound of the formula

R³HN—CHR¹—CO—CH₂—COOR² in which

R¹ is a A, Ar, Ar-alkyl, Het, Het-alkyl, cycloalkyl having 3-7 C atoms which is unsubstituted or mono- or polysubstituted by A, AO and/or Hal, cycloalkylalkyl having 4-11 C atoms or bicycloalkyl having 7-14 C atoms or bicycloalkylalkyl having 8-18 C atoms, R² is H or alkyl having 1-5 C atoms, R³ is H, benzyl, triphenylmethyl, benzyloxycarbonyl, tert.-butyloxycarbonyl or 9-fluorenylmethoxycarbonyl, Ar is phenyl which is unsubstituted or mono- or polysubstituted by A, AO, Hal, CF3, HO, hydroxyalkyl having 1-8 C atoms, H₂N and/or aminoalkyl having 1-8 C atoms or is unsubstituted naphthyl, Het is a saturated or unsaturated 5- or 6.membered heterocyclic radical having 1-4 N, O and/or S atoms which can be fused with a benzene ring and/or mono- or polysubstituted by A, AO, Hal, CF₃, HO, O₂N, carbonyl oxygen, H₂N, HAN, A₂N, AcNH, AS, ASO, ASO₂, AOOC, CN, H₂NCO, HOOC, H₂NSO₂, ASO₂NH, Ar, Ar-alkenyl wherein the alkenyl portion has 2.8 C atoms, hydroxyalkyl and/or aminoalkyl each having 1-8 C atoms and/or whose N and/or S heteroatoms can also be oxidizede.

Hal is F, Cl, Br or I,

Ac is A-CO-, Ar-CO- or A-NH-CO- and

A is alkyl having 1-8 C atoms, by microorganisms to obtain the corresponding secondary alcohols.

2. A process for the enantioselective reduction of a keto compound to give secondary alcohols having an S configuration at the β carbon atom, comprising reducing a keto compound of the formula

R³HN—CHR¹—CO—CH₂—COOR² in which

R¹ is alkyl having 3-8 C atoms, Ar, Ar-alkyl, Het, Het-alkyl, cycloalkyl having 3-7 C atoms which is unsubstituted or mono. or polysubstituted by A, AO and/or Hal, cycloalkylalkyl having 4-11 C atoms or bicycloalkyl having 7-14 C atoms or bicycloalkylalkyl having 8-18 C atoms, R² is H or alkyl having 1-5 C atoms, R³ is H, benzyl, triphenylmethyl, benzyloxycarbonyl, tert.-butyloxycarbonyl or 9-fluoenylmethoxycarbonyl, Ar is phenyl which is unsubstituted or mono- or polysubstituted by A, AO, Hal, CF₃, HO, hydroxyalkyl having 1-8 C atoms, H₂N and/or aminoalkyl having 1-8 C atoms or is unsubstituted naphthyl, Het is a saturated or unsaturated 5 or 6. membered heterocyclic radical having 1-4 N, O and/or S atoms which can be fused with a benzene ring and/or mono- or polysubstituted by A, AO, Hal, CF₃, HO, O₂N, carbonyl oxygen, H₂N, HAN, A₂N, AcNH, AS, ASO, ASO₂, AOOC, CN, H₂NCO, HOOC, H₂NSO₂, ASO₂NH, Ar, Ar-alkenyl wherein the alkenyl portion has 2-8 C atoms, hydroxyalkyl and/or aminoalkyl each having 1-8 C atoms and/or whose N and/or S heteroatoms can also be oxidized, Hal is F, Cl, Br or I, Ac is A—CO—, Ar—CO— or A—NH—CO and A is alkyl having 1-8 C atoms, by microorganisms to obtain the corresponding secondary alcohols.

3. A process according to claim 2, wherein R¹ is benzyl, cyclohexylmethyl, 4-methylcyclohexylmethyl, 4-tert.-butylcyclohexylmethyl, phenyl, p-chlorobenzyl, 2phenylethyl, 2-cyclohexylethyl, 1- or 2-naphthylmethyl, methyl, ethyl, propyl, isopropyl, butyl, isobutyl, sec.-butyl, pentyl or 2- or 3-methylbutyl.

4. A process according to claim 2, wherein $R^2$ is methyl, ethyl, propyl or isopropyl.

5. A process according to claim 2, wherein $R^3$ is H, benzyloxycarbonyl or tert.-butyloxycarbonyl.

6. A process according to claim 2, wherein $R^3$ is not H.

7. A process according to claim 2, wherein said microorganisms contain hydrogen transfer enzymes.

8. A process according to claim 2 wherein said microorganisms are yeasts from the genera Saccharomyces, Candida, Hansenula, Pullularia, Torulopsis and Williopsis.

9. A process according to claim 8, wherein said yeasts are from the genera Hansenula.

10. A process according to claim 2, wherein said yeasts are from the genera Hansenula ciferrii, Hansenula saturnus or Hansenula anomala.

11. A process according to claim 8, wherein said yeasts are Hansenula ciferrii (DSM 70780), Hansenula saturnus (DSM 70278), Saccharomyces uvarum (DSM 70547), Torulopsis candida (DSM 70590) or Hansenula anomala (DSM 70130).

12. A process according to claim 2, wherein $R^1$ is benzyl, 4-methylcyclohexylmethyl or 4-tert.butylcyclohexylmethyl; $R^2$ is methyl or ethyl; and $R^3$ is H, benzyloxycarbonyl or tert.-butyloxycarbonyl.

13. A process according to claim 2, wherein reduction of said keto compound is performed by contacting said keto compound with immobilized microorganism cells capable of reducing the keto compound to form the corresponding secondary alcohol.

14. A process according to claim 2, wherein reduction is performed by adding glucose and said keto compound to a cell-free extract of said microorganisms containing hydrogen transfer enzymes.

15. A process according to claim 7, wherein said microorganisms contain dehydrogenase.

16. A process according to claim 12, wherein said yeast cells contain dehydrogenase.

17. A process according to claim 13, wherein said microorganisms contain dehydrogenase.

18. A process according to claim 2, wherein the selectivity for the biologically active S configuration of secondary alcohol is about 90-99%.

19. A process according to claim 2, wherein microorganisms are grown in a glucose growth medium.

20. In a process for the enantioselective reduction of a keto compound to give secondary alcohols having an S configuration at the β carbon atom, comprising reducing a keto compound of the formula

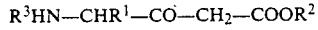

in which
R$^1$ is A, Ar, Ar-alkyl, Het, Het-alkyl, cycloalkyl having 3-7 C atoms which is unsubstituted or mono- or polysubstituted by A, AO and/or Hal, cycloalkylalkyl having 4-11 C atoms or bicycloalkyl having 7-14 C atoms or bicycloalkylalkyl having 8-18 C atoms,
R$^2$ is H or alkyl having 1-5 C atoms,
R$^3$ is H, benzyl, triphenylmethyl, benzyloxycarbonyl, tert.-butyloxycarbonyl or 9 fluorenylmethoxycarbonyl,
Ar is phenyl which is unsubstituted or mono. or polysubstituted by A, AO, Hal, CF$_3$, HO, hydroxyalkyl having 1-8 C atoms, H$_2$N and/or aminoalkyl having 1-8 C atoms or is unsubstituted naphthyl,
Het is a saturated or unsaturated 5- or 6-membered heterocyclic radical having 1-4 N, O and/or S atoms which can be fused with a benzene ring and/or mono- or polysubstituted by A, AO, Hal, CF$_3$, HO, O$_2$N, carbonyl, oxygen, H$_2$N, HAN, A$_2$N, AcNH, AS, ASO, ASO$_2$, AOOC, CN, H$_2$NCO, HOOC, H$_2$NSO$_2$, ASO$_2$NH, AR, AR-alkenyl wherein the alkenyl portion has 2-8 C atoms, hydroxyalkyl and/or aminoalkyl each having 1-8 C atoms and/or whose N and/or S heteroatoms can also be oxidized,
Hal is F, Cl, Br or I,
Ac is A—CO—, Ar—CO— or A—NH—CO— and
A is alkyl having 1-8 C atoms, by microorganisms to obtain the corresponding secondary alcohols, wherein said microorganisms are yeast grown in a glucose growth medium and reduction occurs in a reaction medium containing said yeast in a concentration of 0.5-5%, ethanol in a concentration of 3-10%, said keto compound in a concentration of 0.05-5%, and wherein the duration of incubation in said reaction medium is 24-84 hours.

21. In a process for the enantioselective reduction of a keto compound to give secondary alcohols having an S configuration at the β carbon atom, comprising reducing a keto compound of the formula

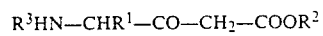

in which
R$^1$ is A, Ar, Ar-alkyl, Het, Het-alkyl, cycloalkyl having 3-7 C atoms which is unsubstituted or mono- or polysubstituted by A, AO, and/or Hal, cycloalkylalkyl having 4-11 C atoms or bicycloalkyl having 7-14 C atoms or bicycloalkylalkyl having 8-18 C atoms,
R$^2$ is H or alkyl having 1-5 atoms,
R$^3$ is H, benzyl, triphenylmethyl, benzyloxycarbonyl, tert.-butyloxycarbonyl or 9 fluorenylmethoxycarbonyl,
Ar is phenyl which is unsubstituted or mono. or polysubstituted by A, AO, Hal, CF$_3$, HO, hydroxyalkyl having 1-8 C atoms, H$_2$N and/or aminoalkyl having 1-8 C atoms or is unsubstituted naphthyl,
Het is a saturated or unsaturated 5- or 6- membered heterocyclic radical having 1-4 N, O and/or S atoms which can be fused with a benzene ring and/or mono- or polysubstituted by A, AO, Hal, CF$_3$, HO, O$_2$N, carbonyl oxygen, H$_2$N, HAN, A$_2$N, AcNH, AS, ASO, ASO$_2$, AOOOC, CN, H$_2$NCO, HOOC, H$_2$NSO$_2$, ASO$_2$NH, Ar, Ar-alkenyl wherein the alkenyl portion has 2-8 C atoms, hydroxyalkyl and/or aminoalkyl each having 1-8 C atoms and/or whose N and/or S heteroatoms can also be oxidized,
Hal is F, Cl, Br or I,
Ac is A—CO—, Ar—CO or A—NH—CO— and
A is alkyl having 1-8 C atoms, by microorganisms to obtain the corresponding secondary alcohols, wherein microorganisms are yeast grown in a glucose growth medium and reduction occurs in a reaction medium containing yeast in a concentration of 1-2%, ethanol in a concentration of 3-10%, said keto compound in a concentration of 0.1–0.2%, and wherein the duration of incubation in said reaction medium is 48–72 hours.

22. A process according to claim 2, wherein the yield of secondary alcohols is about 50–98%.

23. A process for the enantioselective reduction of a keto compound to give secondary alcohols having an S configuration at the β carbon atom, comprising reducing a keto compound of the formula $$R^3HN-CHR^1-CO-CH_2-COOR^2$$

in which
- $R^1$ is A, Ar, Ar-alkyl, Het, Het-alkyl, cycloalkyl having 3–7 C atoms which is unsubstituted or mono- or polysubstituted by A, AO and/or Hal, cycloalkylalkyl having 4–11 C atoms or bicycloalkyl having 7–14 C atoms or bicycloalkylalkyl having 8–18 C atoms,
- $R^2$ is H or alkyl having 1–5 C atoms,
- $R^3$ is H, benzyl, triphenylmethyl, benzyloxycarbonyl, tert-butyloxycarbonyl or 9 fluorenylmethoxycarbonyl,
- Ar is phenyl which is substituted or mono- or polysubstituted by A, AO, Hal, $CF_3$, HO, hydroxyalkyl having 1.8 C atoms, $H_2N$ and/or aminoalkyl having 1–8 C atoms or is unsubstituted naphthyl,
- Het is a saturated or unsaturated 5. or 6.membered heterocyclic radical having 1-4 N, O and/or S atoms which can be fused with a benzene ring and/or mono- or polysubstituted by A, AO, Hal, $CF_3$, HO, $O_2N$, carbonyl oxygen, $H_2N$, HAN, $A_2N$, AcNH, AS, ASO, $ASO_2$, AOOC, CN, $H_2NCO$, HOOC, $H_2NSO_2$, $ASO_2NH$, AR, AR-alkenyl wherein the alkenyl portion has 2–8 C atoms, hydroxyalkyl and/or aminoalkyl each having 1–8 C atoms and/or whose N and/or S hetero atoms can also be oxidized,
- Hal is F, CL, Br or I,
- Ac is A—CO—, Ar—CO— or A—NH—CO— and
- A is alkyl having 1–8 C atoms, by microorganisms to obtain the corresponding secondary alcohols wherein reduction is performed by preparing an ethanol solution of said keto compound and adding said ethanol solution to a suspension of yeast cells wherein said yeast cells contain hydrogen transfer enzymes.

24. A process according to claim 23, wherein said microorganisms contain dehydrogenase.

* * * * *